United States Patent [19]

Sapega et al.

[11] Patent Number: 4,922,897
[45] Date of Patent: May 8, 1990

[54] APPARATUS AND METHOD FOR RECONSTRUCTIVE SURGERY

[75] Inventors: Alexander A. Sapega, Philadelphia; Ray A. Moyer, Dresher, both of Pa.; Donald Rose, New York, N.Y.

[73] Assignee: Temple University, Philadelphia, Pa.

[21] Appl. No.: 180,345

[22] Filed: May 13, 1988

Related U.S. Application Data

[62] Division of Ser. No. 915,157, Oct. 3, 1986, abandoned.

[51] Int. Cl.⁵ .................................................. A61F 5/04
[52] U.S. Cl. .......................................... 606/80; 606/73; 606/75
[58] Field of Search ......... 128/92 V, 92 VZ, 92 VW, 128/92 VD, 92 VL, 92 YF, 92 YJ, 92 YC, 92 YD, 774, 305.1, 92 R, 92 VK

[56] References Cited

U.S. PATENT DOCUMENTS

| | | | |
|---|---|---|---|
| 4,226,025 | 10/1980 | Wheeler | 128/774 |
| 4,257,411 | 3/1981 | Cho | 128/92 VD |
| 4,312,337 | 1/1982 | Donohue | 128/92 VD |
| 4,414,985 | 11/1983 | Myer | 128/774 |
| 4,444,180 | 4/1984 | Schneider | 128/92 VD |
| 4,535,768 | 8/1985 | Hourahane | 128/305.1 |

OTHER PUBLICATIONS

Wolf, Richard, Anterior Cruciate Ligament Reconstruction, (New York, 1986), pp. 1–20.
OSI Isometric ACL Reconstruction System.
Acufex Arthroscopic Drill System, Indianapolis, Indiana.
Lipscomb Brant, Lipscomb Anderson Drill Guide, Memphis, Tennessee, 1983, pp. 1–8.

Primary Examiner—Robert A. Hafer
Assistant Examiner—Michael Brown
Attorney, Agent, or Firm—Austin R. Miller

[57] ABSTRACT

A method and apparatus for the permanent surgical reconstruction of the anterior cruciate ligament in the human knee, which will stabilize the tibia and femur relative to each other and restore a full range of motion to the knee, by precisely locating the ends and angular relationship of a replacement ligament within the knee joint, at bone attachment sites such that the degree of shortening and lengthening experienced by the replacement ligament over the range of joint motion is either as close to zero (isometric) as possible, or closely matches that of the natural uninjured ligament (physometric), whichever the surgeon feels is most desirable.

12 Claims, 5 Drawing Sheets

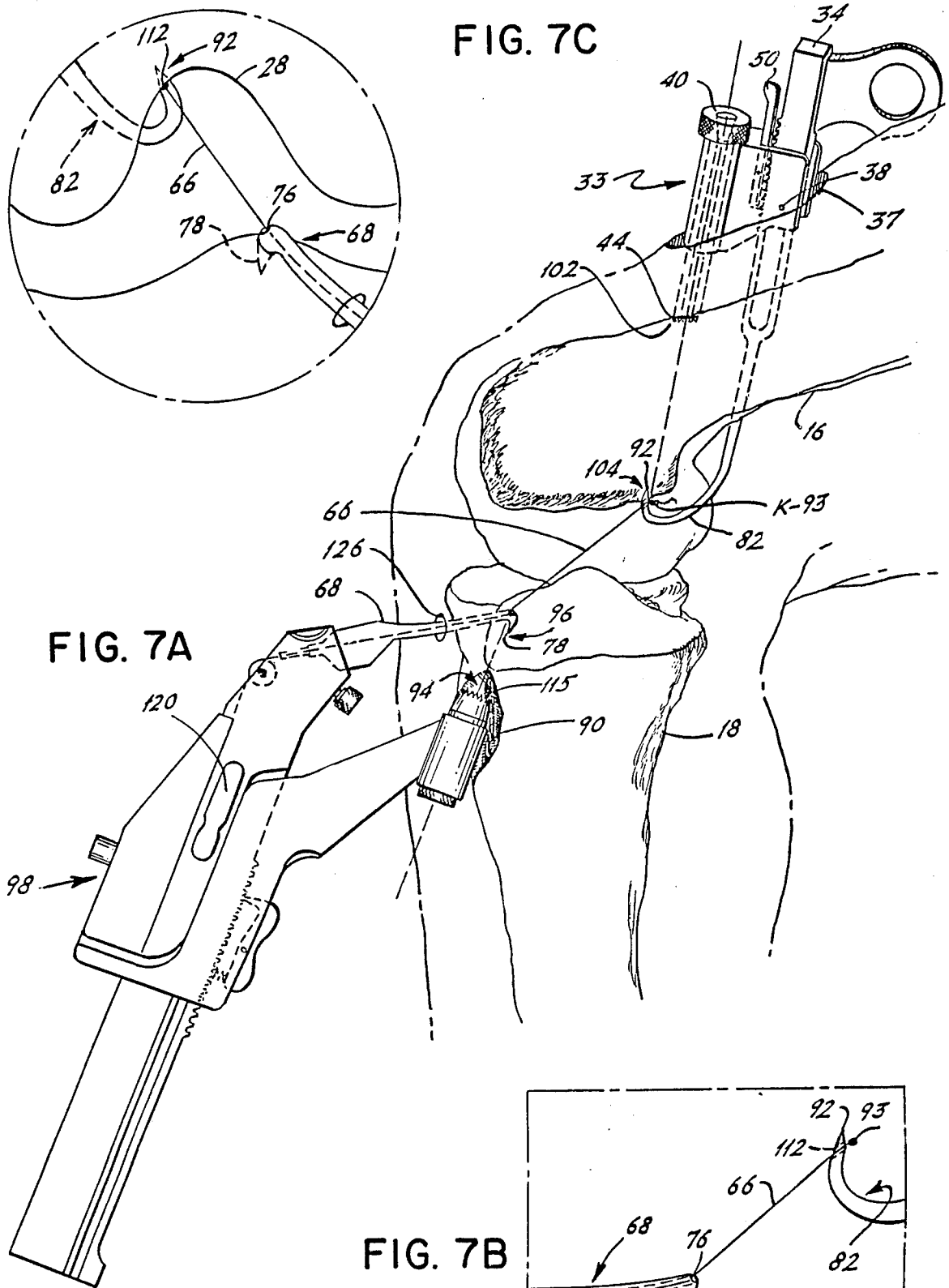

APPARATUS AND METHOD FOR RECONSTRUCTIVE SURGERY

This is a division of application Ser. No. 915,157 filed Oct. 3, 1986 now U.S. Pat. No. 4739 751.

BACKGROUND OF THE INVENTION

This invention relates to a method for human knee ligament reconstruction, particularly the anterior cruciate ligament.

FIELD OF THE INVENTION

The human knee is continually being subjected to a variety of stresses and strains. Because of the physical demands that are often placed upon it, along with its natural vulnerability, injury to various portions of the joint are quite common. Thousands of knee injuries occur each year.

One particularly severe knee injury is damage to the anterior cruciate ligament. This can happen through a variety of contact and noncontact injury mechanisms, especially when severe twisting occurs. The anterior cruciate ligament is paired with the posterior cruciate ligament, functioning as bone-to-bone connecting bands between the ends of the femur and tibia inside the knee joint. They cross each other as the anterior cruciate ligament traverses from a frontal portion of the end of the tibia to a rearward portion of the end of the femur. Conversely, the posterior cruciate ligament traverses from a rearward portion of the end of the tibia to a frontal portion of the end of the femur.

These ligaments maintain stability in the joint by restricting forward and rearward transverse movement of the end of the tibia in relation to the femur.

There are a variety of problems facing the surgeon in attempting repair of a ruptured anterior cruciate ligament. Attempts to repair this ligament by simply sewing the ruptured ends back together have met with very limited success for many reasons, including the fact that a viable ligament requires the continual flow of blood therethrough, and the fact that when the ligament tears, the ends tend to fray greatly. Current methods are incapable of sorting out, rearranging and sewing together the many frayed fasicles that comprise the ligament, and solid healing is very unreliable.

Attempts to augment primary sewing with supplementary graft tissue have therefore been made. Augmentation places graft tissue, typically a piece of tendon, alongside the sewn ligament to add to the overall strength of the repair. However, there are significant limitations to the augmentation process. It has been discovered that a primary sewing repair with an augmentation procedure must be done quickly after the rupture takes place. Furthermore, augmentation has not been able to repair the ligament to an extent where natural knee capabilities are satisfactorily approached. In many instances, the day-to-day use of the knee remains functionally limited, particularly in physical fitness or recreational pursuits. One specific problem is that the ligament graft tissue can only be placed adjacent to, and not at, the site of the repaired anterior cruciate ligament. Therefore, the graft's mechanical function does not truly duplicate that of the normal anterior cruciate ligament.

In cases where it is not deemed satisfactory or practical to either sew or sew and augment the ligament, attempts have been made to replace or reconstruct the ligament entirely, typically with a graft taken from a knee tendon. Attempts at such reconstruction have met with further problems. In order to duplicate the mechanical function of the original anterior cruciate ligament, it is essential that any replacement be properly placed within the knee joint at the exact site of the original anterior cruciate ligament. It has been found that a variation of only several millimeters from the normal ligament attachment position on the tibia, and especially the femur can result in the new ligament being too tight in some knee joint positions and too loose in others. In addition, the anterior cruciate ligament has a complex macrostructure that is flat to avoid in cross section, rather than round. This creates great difficulties in trying to reconstruct the entire anterior cruciate ligament with a tendon graft which is typically cylindrical in shape. A single cylindrical graft can only accurately reconstruct one of the two major portions of the anterior cruciate ligament (anteromedial and posterolateral bands). A pair of cylindrical grafts, attached to adjacent bone sites that match the normal attachment points of the anteromedial and posterolateral bands to the tibia and femur, are required to recreate the complete structure and function of the anterior cruciate ligament. Due to the technical difficulties involved in properly locating all four bone attachment sites in such a double-banded reconstructive procedure, however, it is seldom attempted. A less technically exacting and commonly employed alternative is to attempt to reconstruct only the anteromedial portion with a single tendon graft, as this portion of the ligament is believed to be the more functionally important of the two.

In such reconstructive procedures it is known to drill tunnels through the ends of the femur and the tibia. The replacement ligament is typically inserted through one tunnel, then across the knee joint, then out through the other tunnel and then secured on the outside to each bone above and below the knee. If the tunnels are drilled in any but the optimum positions as they enter the interior joint cavity, the tendon graft's position does not closely duplicate that of the normal anterior cruciate ligament, producing either too much or too little ligament tightness at certain joint positions. If the joint is too loose at a given knee joint position, this permits excessive transverse sliding movement between the femur and tibia. If it is too tight at any joint position, this will result either in failure of the replacement ligament due to overstress, or a restriction of the knee's range of motion.

Determining the proper placement for these bone tunnels has been most difficult. This is due in part to the fact that the anatomic landmarks within the knee joint that indicate where the damaged anterior cruciate ligament was attached to the tibia and femur are often obscure and misleading due to the severe damage of the ligament, with stump fraying and disintegration. This is especially difficult for the femur where the ideal tunnel site resides in the intercondylar notch toward the rearward side. When unguided visual judgment is employed to determine the locations for the tunnel entrances into the joint cavity, consistently accurate tunnel placement has been virtually impossible. Moreover, there has been a lack of surgical apparatus capable of positively identifying the optimum tunnel sites.

Guide instruments exist which are intended to indicate the optimum femoral tunnel entrance site according to fixed distances from specific index landmarks within the joint. However, their accuracy is very inconsistent and is limited by the ability of the surgeon to locate the index landmarks precisely, and by the fact that the shape and size of the femur is known to vary from patient to patient.

Another method involves drilling narrow bone channels in the general area of normal ligament attachment on a trial and error basis until satisfactory sites are found, and then widening the desired channels to receive the graft. The method requires the surgeon to thread a suture or wire through each set of pilot channels as if it were a graft, fix it to bone at one channel's external exit, place tension on the opposite end, and measure the degree of suture or wire excursion in and out of the external exit of the other bone channel as the surgeon moves the knee through a range of motion. The excursion indicates the amount of suture shortening or lengthening that would have occurred within the joint had the suture been fixed to bone at both ends, as the tendon graft will be. What this method actually measures is the change in separation distance between internal channel exits, as the tibia and femur pivot with respect to one another. In testing prospective bone tunnel sites in this manner, many surgeons currently desire their graft attachment sites to be "isometric" with respect to one another, that is, no change in attachment site distance as the tibia and femur pivot and thus no future graft tightening or loosening as the knee is flexed. This lack of change in separation distance occurs despite the fact that no part of the normal anterior cruciate ligament exhibits isometric mechanical behavior.

Other surgeons are likely to prefer to duplicate normal anterior cruciate mechanics as closely as possible, by selecting graft attachment (tunnel entrance) sites that demonstrate the natural pattern of approximation and separation as the knee is flexed, thus creating "physiometric" graft behavior as set forth for the first time herein.

Regardless of the criteria for tunnel site acceptability employed, the above pilot channel and testing suture method for selecting the desired tunnel entrance sites is not suited for routine use. This is because repeated drilling, suture threading, and excursion testing is tedious and time-consuming, and unwanted extra bone holes are often created.

A further problem is that not only is it extremely difficult to locate what are thought to be the optimal tunnel sites, but once the tunnels are drilled, the graft will not stay centered within the tunnel. This occurs because the graft tissue is pliable and can distort depending upon the stresses it encounters. As the ligament graft courses though one tunnel, across the knee and then through the other tunnel, it will typically change direction when bending around the corners of the tunnel entrances within the joint cavity. The pressure exerted by the edge of a tunnel entrance flattens the ligament as the graft turns the corner, causing it to shift off center in the channel as it exits. This effectively changes the graft's flexural (bone fixation) points, thus altering the mechanical behavior of the ligament from what it would be if it were centered in the tunnel. This can result in the problems previously discussed. Therefore, further uncertainty is introduced because even if the surgeon can locate the proper tunnel locations there is no way to keep the new ligament centered at those points.

OBJECTS OF THE INVENTION

Thus, it is an object of the present invention to provide a method of reconstruction of the anterior cruciate ligament in the human knee such that abnormal forward transverse sliding of the tibia on the femur is stabilized while permitting these bones to pivot with respect to each other at the joint in a manner comparable to that prior to injury.

It is also an object of the present invention to provide a means, in knees of all sizes, to quickly, easily, and precisely locate the particular tibial and femoral bone tunnel sites that will endow the ligament graft with either isometric or physiometric mechanical behavior, whichever the surgeon prefers, without the need for drilling and testing preliminary bone channels.

It is a further object of the present invention to allow a surgeon to identify the physiometric tunnel sites for, and then reconstruct, either a single specific band of the anterior cruciate ligament with a single graft, or to perform the above for both main bands (anteromedial and posterolateral) of the anterior cruciate ligament by employing two closely approximated but separate bone tunnels in each bone and two separate ligament grafts therethrough.

It is further object of the present invention to provide a method of reconstruction of the anterior cruciate ligament that can be performed either with traditional open incision techniques or newer, arthroscopically assisted methods.

It is yet a further object of the present invention to provide apparatus that functions as a bone tunnel drill guide and that will enable the surgeon to drill the needed bone tunnels such that they enter the joint in slightly offset locations from the desired graft fixation points, in a manner that compensates for the typical off-center shift of the ligament graft as it exits the bone tunnel.

Other objects and advantages of the present invention will become readily apparent to those skilled in the art by detailed descriptions of the preferred embodiments and the appended claims.

SUMMARY OF THE INVENTION

The present invention provides a method and apparatus for the permanent surgical reconstruction of the anterior cruciate ligament in the human knee, that given a suitable ligament graft, will restore joint stability while allowing a full range of motion to the knee, by quickly and precisely locating either the isometric or physiometric attachment points for the replacement ligament within the joint, whichever is preferred, without the need for drilling and testing preliminary bone channels.

BRIEF DESCRIPTION OF THE DRAWINGS

FIG. 7A is a side perspective view of a human knee joint similar to that in FIG. 2, having both the tibial and rearwardly introduced femoral drill locating and orientation apparatus applied to the tibia and femur according to one method of this invention.

FIG. 7B is an exploded side view of the intra-articular portion of the tibial and rearwardly introduced femoral drill locating and orientation apparatus, showing one possible route of passage and method of fixation of a connecting wire between the two apparatus.

FIG. 7C is an exploded front elevational view depicting the typical positional relationships of the intra-articular portions of the tibial and rearwardly introduced femoral drill locating and orientation apparatus of the method of this invention, as applied to the end portions of the tibia and femur.

DETAILED DESCRIPTION OF THE DRAWINGS

Figure 1:
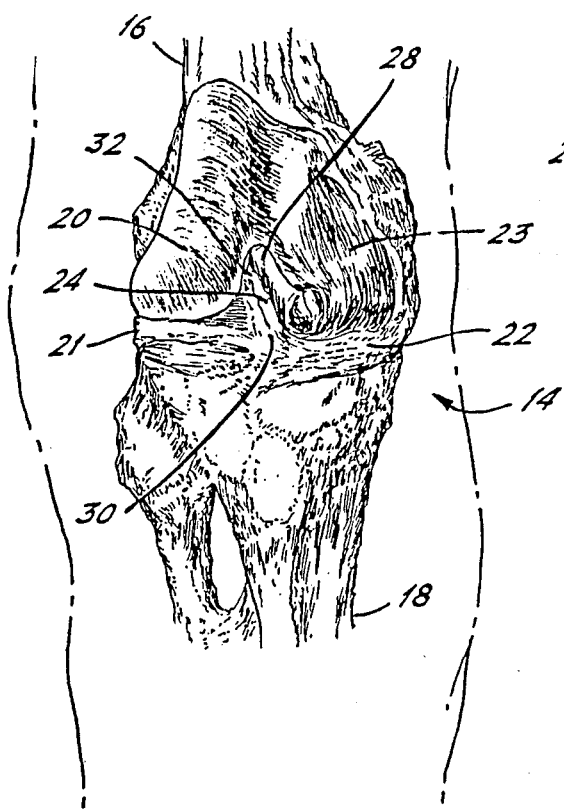
FIG. 1 is a front elevational view of a partially bent, typical human knee joint having skin and muscle tissue removed along with the patella and all exterior ligaments, for ease of view of the anterior cruciate ligament.

Although specific embodiments of the invention have been selected for illustration in the drawings and although specific terms will be used in the description which follows, such selection and terms are not intended to limit the scope of the invention, which is defined in the appended claims.

Referring to FIG. 1, knee joint 14 is formed at the lowermost portion of femur 16 and the uppermost portion of tibia 18. Outer condyle 20 of femur 16 is in contact with tibia 18 and external semi-lunar cartilage 21. Inner condyle 23 resides adjacent outer condyle 20 and also contacts tibia 18 and inner semi-lunar cartilage 22. Intercondylar notch 28 separates condyles 20 and 23. Tibia 18 and femur 16 pivot at their contact points. One of the ligaments that connect tibia 18 and femur 16 together is anterior cruciate ligament 24 connected to tibia 18 at attachment site 30 and passes upwardly, rearwardly and outwardly and connects with femur 16 at the inner portion 32 of outer condyle 20, at the rear of intercondylar notch 28.

Figure 2:
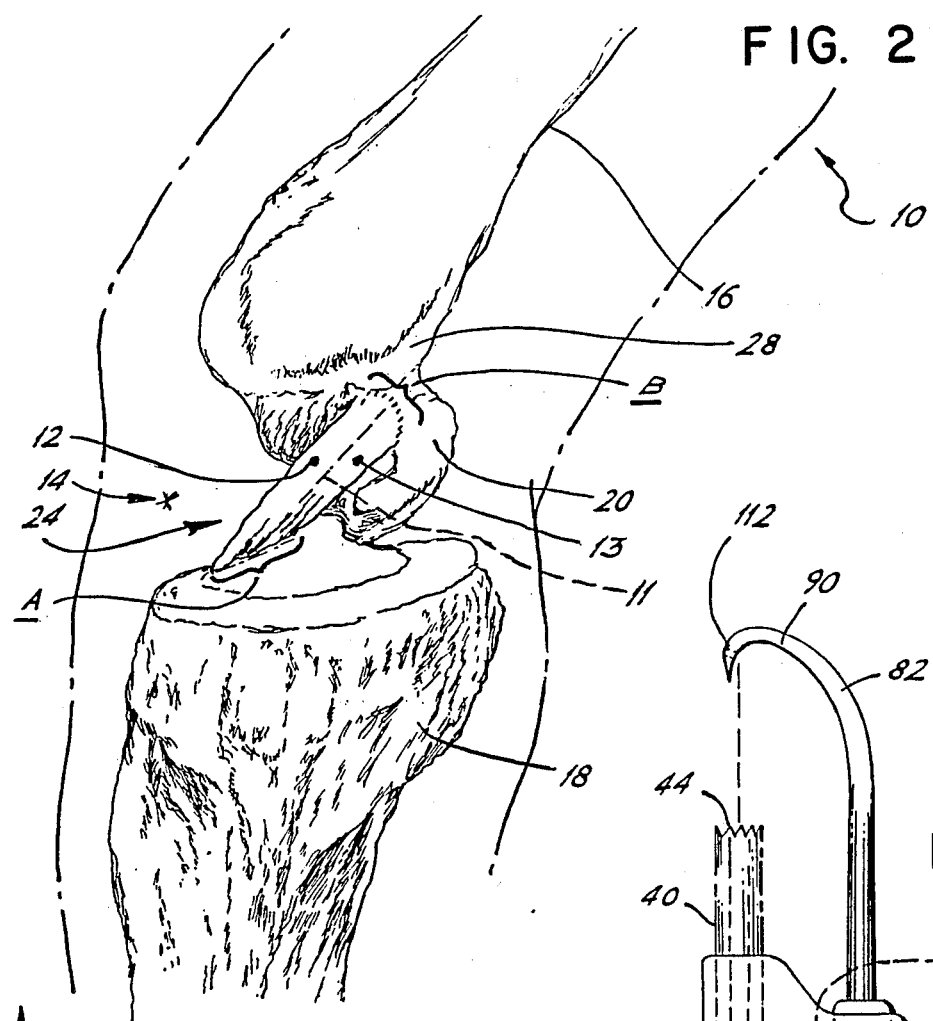
FIG. 2 is a side perspective view of a portion of a typical knee joint partly in section with the inner condyle of the femur removed along with all the external ligaments and the patella, for ease of view of both major bands of the anterior cruciate ligament.

In FIG. 2 leg 10 is slightly bent at knee 14 formed by femur 16 and tibia 18. Outer condyle 20 contacts tibia 18 and external semi-lunar cartilage 21 (see FIG. 1). Inner condyle 23 from FIG. 1 has been removed from the showing in the drawing in order to facilitate viewing intercondylar notch 28 and anterior cruciate ligament 24 from the side. Anterior cruciate ligament 24 passes from its attachment to tibia 18 along area A, upwardly, rearwardly and outwardly into intercondylar notch 28 and attaches to femur 16 along area B. The two main portions of the anterior cruciate ligament, the anteromedial 12 and posterolateral 13 bands, are shown as separated by dashed line 11.

Figure 3:
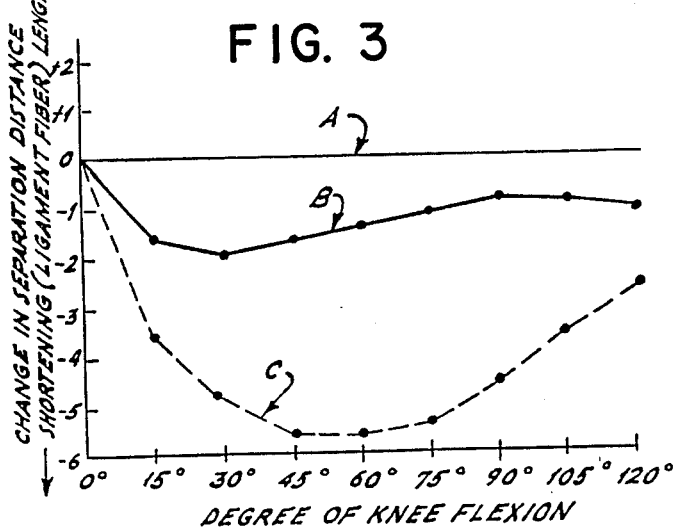
FIG. 3 is a graph of the mechanical behavior (fiber lengthening-shortening) experienced by the two different bands of the normal anterior cruciate ligament as the knee moves through its range of motion.

FIG. 3 is a graph depicting the typical change in length, as indicated by the change in tibial and femoral attachment site separation distance, exhibited by the two major bands of the normal anterior cruciate ligament in the uninjured state as the knee moves through its range of motion. As can be seen from Curves B (anteromedial) and C (posterolateral) the mechanical behavior of these two bands is not the same. Neither one exhibits isometric behavior, theoretically illustrated by line A.

Figure 4:
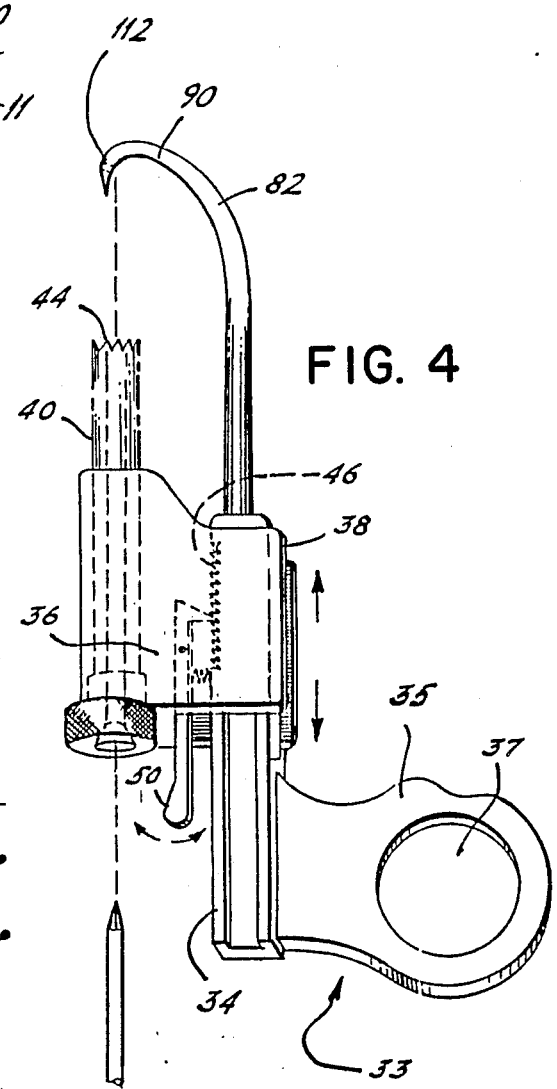
FIG. 4 depicts a side elevational view of a femoral drill locating and orientation apparatus according to the method of this invention intended for partial introduction into the knee joint from the rear and lateral side.

FIG. 4 depicts one embodiment of a rearwardly introduced, femoral drill locating and orientation device, hereinafter referred to for convenience and brevity as posterior femoral guide 33 according to the present invention. The posterior femoral guide 33 is provided with a guide beam 34. A drill sleeve assembly 36 is mounted on guide beam 34 with connector 38 which slides along portions of the length of guide beam 34. A drill sleeve 40 is screwed or removably mounted into drill sleeve assembly 36. Drill sleeve 40 can either receive a drill or a pointed drill guide pin, which, once inserted into bone through posterior femoral guide 33, can be over-reamed with a cannulated drill to create the final bone tunnel. Teeth 44 are provided so as to impart a better grip onto the bone when posterior femoral guide 33 is applied.

Connector 38 slides along guide beam 34 and over ratchet teeth 46. Sliding action may be actuated or precluded by application of locking means 50 into ratchet teeth 46. Posterior femoral guide 33 is further provided with a handle 35 having finger hole 37 to assist the operator in positioning posterior femoral guide 33 into the desired position after it has been introduced into the knee. Guide beam 34 also has a femoral aimer arm 82 attached thereto, the function of which will become apparent hereinafter.

Figure 5:
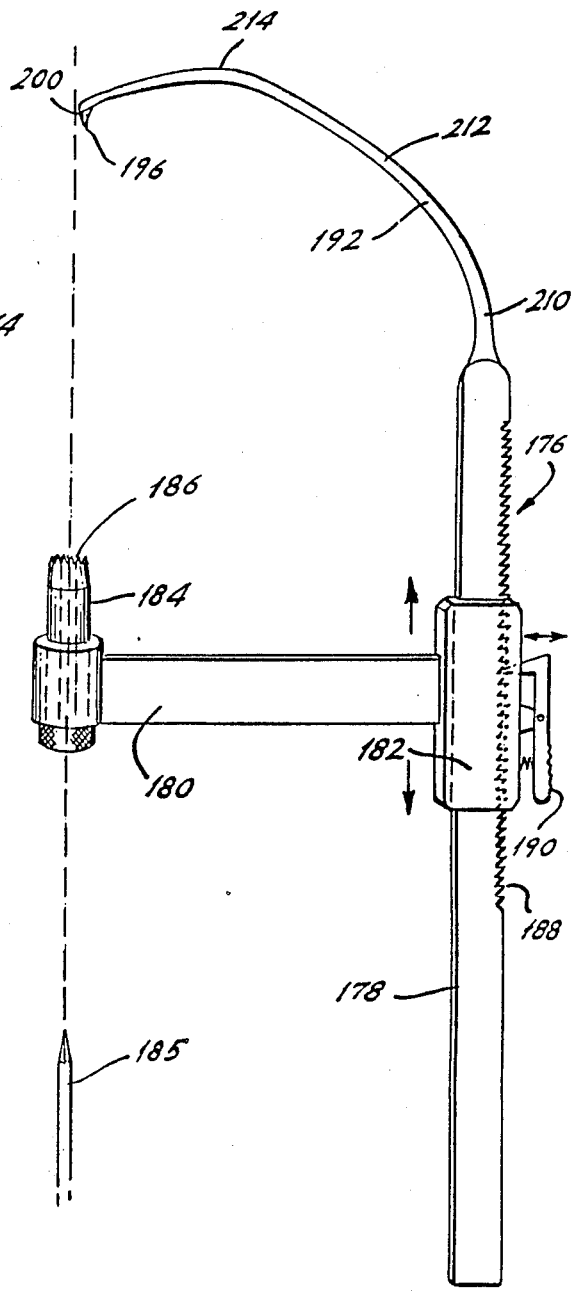
FIG. 5 depicts a side elevational view of alternative femoral drill locating and orienting apparatus, according to the method of this invention, intended for partial introduction into the knee joint from the front.

FIG. 5 depicts one embodiment of an alternative anteriorly introduced femoral drill locating and orientation device, hereinafter referred to for convenience and brevity as anterior femoral guide 176, in accordance with the present invention. The anterior femoral guide 176 is provided with a guide beam 178. A drill sleeve assembly 180 is mounted on guide beam 178 with connector 182 which slides along portions of the length of guide beam 178. A drill sleeve 184 is screwed or removably mounted into drill sleeve assembly 180. Drill sleeve 184 can either receive a drill 185 or a pointed drill guide pin, which once inserted into the bone through anterior femoral guide 176, can be over-reamed with a cannulated drill to create the final bone tunnel. Teeth 186 are provided so as to impart a better grip onto the bone when anterior femoral guide 176 is applied.

Connector 182 slides along guide beam 178 and over ratchet teeth 188. Sliding action may be actuated or precluded by application of spring-loaded locking means 190 into ratchet teeth 188. Anterior femoral guide 176 is further provided with aimer arm 192 attached thereto.

Aimer arm 192 has a mounting portion 210 suitable for mounting onto guide beam 178. An intermediate portion 212 angles away from mounting portion 210 at an obtuse angle angled at about 125°. A curved region 214 is provided between intermediate portion 212 and a pointed tip 196 having wire channel 200.

Figure 6C:
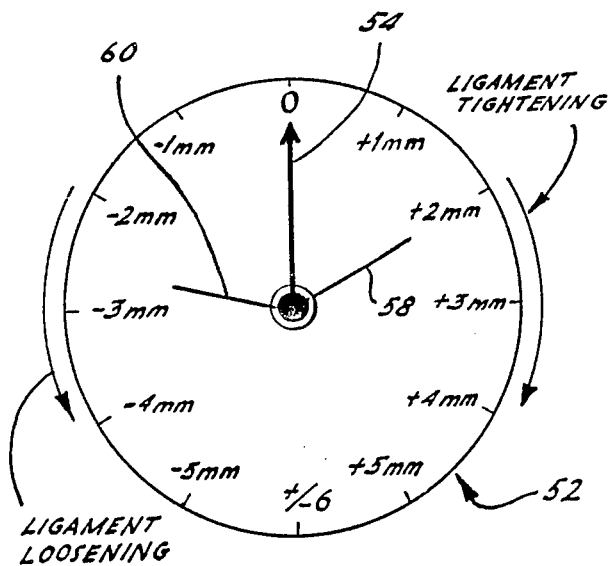
FIG. 6C is an exploded view of the excursion gauge face from FIG. 6B.
Figure 6A:
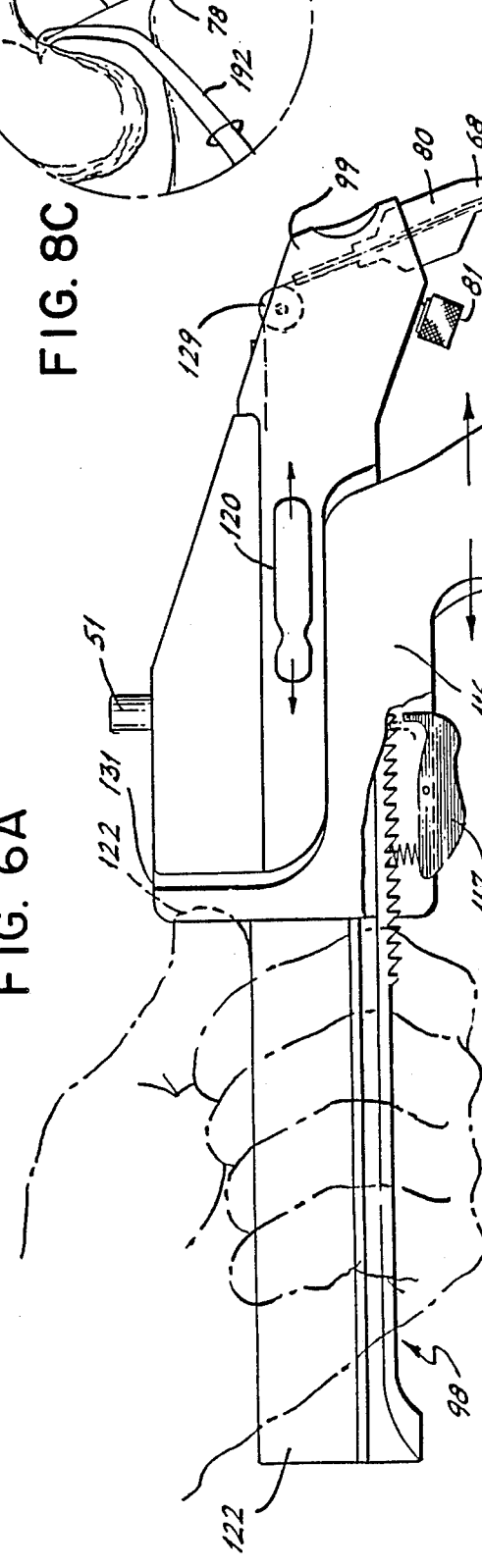
FIG. 6A is a side elevational view of a tibial drill locating and orientation apparatus according to the invention.
Figure 6B:
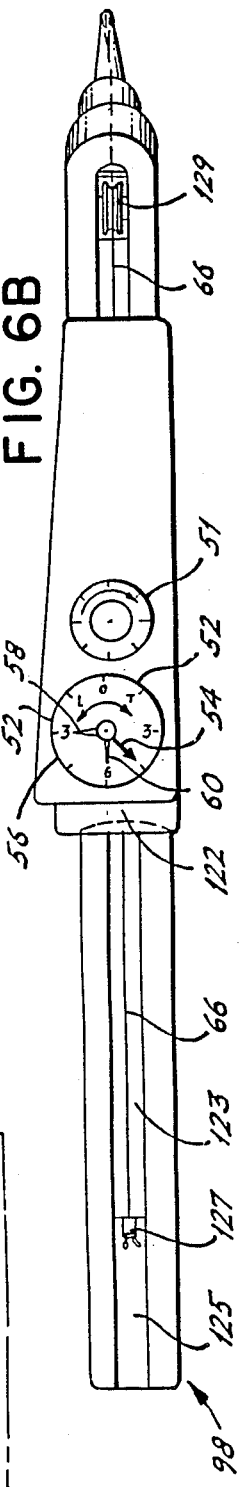
FIG. 6B is a top plan view of the tibial drill locating and orientation apparatus from FIG. 6A.

FIGS. 6A and 6B depict one embodiment of a frontally introduced tibial drill locating and orientation device, hereinafter referred to for convenience and brevity as tibial guide 98, according to the present invention. The tibial guide 98 is provided with a guide beam 122. A drill sleeve assembly 121 is mounted on guide beam 122 via grooves in connector 116 which slides along portions of the length of guide beam 122. A drill sleeve 114 is screwed or removably mounted sliding drill sleeve assembly 121 and can receive either a drill bit 119 or a drill guide pin which is inserted therein. Teeth 115 are provided so as to impart a better grip onto the bone when tibial drill guide 98 is applied.

Tibial guide 98 further contains a finger actuated ratchet release lever 117 to release drill sleeve assembly 121 from guide beam 122 for sliding therealong. Lock 120 releases shuttle 123 for sliding movement within groove 125 of guide beam 122. Shuttle 123 is connected to spring means (not shown) within guide beam 122 to exert tension on wire 66 as partially designated in FIG. 6A by broken line 127. In operation, wire 66 connects to shuttle 123 on its proximal end at tying post 127 and extends along groove 125 in guide beam 122 to wheel 129. After passing over wheel 129, wire 66 then continues through the head region 99 of guide beam 122 to enter an interior channel in tibial aimer arm 68, continuing therethrough to exit at hole 76. If tension is placed on wire 66 external to tibial aimer arm 68, the wire will slide out of exit hole 76, pulling spring-loaded shuttle 123 forward toward head region 99 of guide beam 122. If wire 66 is released externally, shuttle 123 will retract, causing wire 66 to slide back into tibial aimer arm 68.

Drill sleeve assembly 121 is easily slid forward toward aimer arm 68 on guide beam 122 by applying thumb pressure on thumb post 131. Each increment in position automatically is held by spring loaded ratchet lever 117, for ease of application to tibia 18 with one hand. Furthermore, ratchet lever 117 can easily be depressed to unlock assembly 121 by the same finger that can be used to slide assembly 121 back away from aimer arm 68.

Excursion gauge 52 (see FIG. 6B and 6C) is rigidly mounted on guide beam 122 to measure the degree to which wire 66 is pulled in and out of tibial aimer arm 68. Gauge 52 is coupled to sliding shuttle 123 within guide beam 122, which is in turn connected to wire 66 at tying post 127. Active gauge marker 54 directly indicates the linear excursion of shuttle 123, and moves passive gauge markers 58 and 60, which remain at the extreme positions of active markers 54 motion in either direction. Re-set knob 51 repositions all markers 54, 58 and 60 to the zero position as shown in FIG. 6C.

It should be appreciated however, that while gauge 52 has been described in a particular form, the excursion measurements can be achieved by a number of alternative gauge means such as electronic or the like.

In FIG. 7A, tibial guide 98 is shown applied to tibia 18 in a typical fashion. Drill sleeve teeth 115 are in contact with tibia 18 at site 94 approaching the tibia through incision 90. Tibial aimer arm 68 extends into the knee joint via a frontal approach, through portal 126 and contacts tibia 18 at site 96 in an area approximating the connecting area of anterior cruciate ligament 24 to tibia 18.

In accordance with one method of application of one embodiment of the apparatus, posterior femoral guide 33 is mounted onto femur 16 with femoral aimer arm 82 entering intercondylar notch 28 from a lateral, rearward approach. Drill sleeve teeth 44 grip the femur 16 externally at site 102, approaching the femur through incision 37. Femoral aimer arm 82 extends into the intercondylar notch 28 and contacts femur 16 at site 104 in an area approximating the connecting area of anterior cruciate ligament 24 to femur 16. As with tibial guide 98, posterior femoral guide 33 includes a guide beam 34, a slidable connector 38, lock 50 and drill sleeve 40. Femoral guide 33 is not equipped with a wire excursion measuring means as is tibial guide 98. However, it is possible that femoral guide 33 be so equipped, with tibial guide 98 having or not having such wire excursion measuring means.

The placement of the tips of aimer arms 82 and 68 at sites 96 and 104 can be performed by the surgeon either by viewing the interior of the knee joint through an open incision, or with an arthroscope in an arthroscopic procedure, which arthroscope (not shown) extends into the knee joint.

FIG. 7B shows an exploded view of tips 78 and 92 of the respective aimer arms 68 and 82. Wire 66 extends from hole 76. Tip 92 has wire passageway 112 into which the end of wire 66 is inserted. The end of wire 66 is inserted through wire passageway 112 and knotted at knot 93 thereby connecting the respective aimer arms.

FIG. 7C shows the positional relationships of aimer arms 68 and 82 with wire 66 when they are applied to the upper portion of tibia 18 and lower portion of femur 16. Wire 66 exits hole 76 in tip 78 of tibial aimer arm 68 and extends directly to tip 92 of femoral aimer arm 82, to which wire 66 is affixed. Tibial and femoral aimer arms 68 and 82 are applied to tibia 18 and femur 16 such that sites 96 and 104 (see FIG. 7A) are occupied by tips 78 and 92, respectively.

When aimer arm tips 78 and 92 are embedded into tibia 18 and femur 16 at sites 96 and 104, respectively, any change in distance between sites 96 and 104 that occurs as the surgeon moves the knee through its range of motion causes wire 66 to slide in and out of tibial aimer arm 68. This in turn causes an equal degree of excursion of the sliding shuttle 123 within guide beam 122, which is then read by the surgeon on gauge 52 of tibial guide 98. The resulting excursion profile indicates the degree of ligament tightening or loosening that would occur if a ligament graft were attached to the tibia and femur at the sites where tips 78 and 92 are embedded.

If the surgeon deems the excursion profile of these sites acceptable, then drill guides 33 and 98 are employed as hereinbefore described in order to drill the bone tunnels from outside in, thereby leading to points that are intentionally slightly offset from the sites where the aimer tips are embedded. If the surgeon deems the excursion profile as unacceptable, one or both of the aimer arm tips may be moved slightly. Typically, movement of a number of millimeters within the region of sites 96 and 104 is undertaken. The aimer arm tips, after being reapplied to the bone surfaces, allow another excursion profile to be obtained.

It has been found that each site can be tested in less than about one minute. This process continues until the desired wire excursion (future graft tightening and loosening) profile is obtained. The tunnels are then drilled. If the surgeon desires to reconstruct both the anteromedial and posterolateral band portions of the anterior cruciate ligament with two separate grafts this process is performed twice. Once for each portion, using their distinctly different tightening-loosening profiles (as shown in FIG. 3) as a guide in finding appropriate tunnel sites.

Tibial and femoral guides 98 and 33 eliminate guess work in tunnel site selection and systematically allow the surgeon to achieve either isometric or natural (physiometric) ligament mechanical behavior, whichever is preferred.

In one possible manner of applying drill guides 98 and 33, wire 66 is first tied onto the end of a curved introducing rod (not shown). A portion of the length of this introducing rod with affixed wire 66, is pushed into the knee joint through tibial guide portal 126 and brought through intercondylar notch 28 to the rear of the joint and is pushed out above and posteriorly through incision 37. Wire 66, now also crossing the knee and exiting through incision 37, is untied from the introducing rod and inserted through femoral aimer arm tip channel 112 and knotted into knot 93, thus affixing wire 66 to aimer tip 92.

The introducing rod is equipped with a hole in its tip slightly larger than tip 92 of femoral aimer arm 82, which catches tip 92 upon insertion therein. The introducing rod is withdrawn back through incision 37, and back across the joint, thereby pulling femoral aimer arm 82 into intercondylar notch 28. The end of the introducing rod is disengaged from the tip of aimer arm 82 and then withdrawn completely from the knee, leaving only wire 66 exiting from portal 126. This end of wire 66 is then introduced into hole 76 of tibial aimer arm 68 and threaded down its internal channel, over wheel 129, down groove 125, and toward tying post 127. Tibial aimer arm 68 is then slid over wire 66 into the intercondylar notch through portal 126. Both drill guides 33 and 98 are then applied to the femur 16 and tibia 18, as shown in FIG. 7A, and then wire 66 is tensioned and tied to shuttle 123 at tying post 127.

It should be appreciated however, that inserting wire 66 into the knee and applying drill guides 33 and 98 to the bones can be achieved in a number of alternative manners.

Figure 8C:
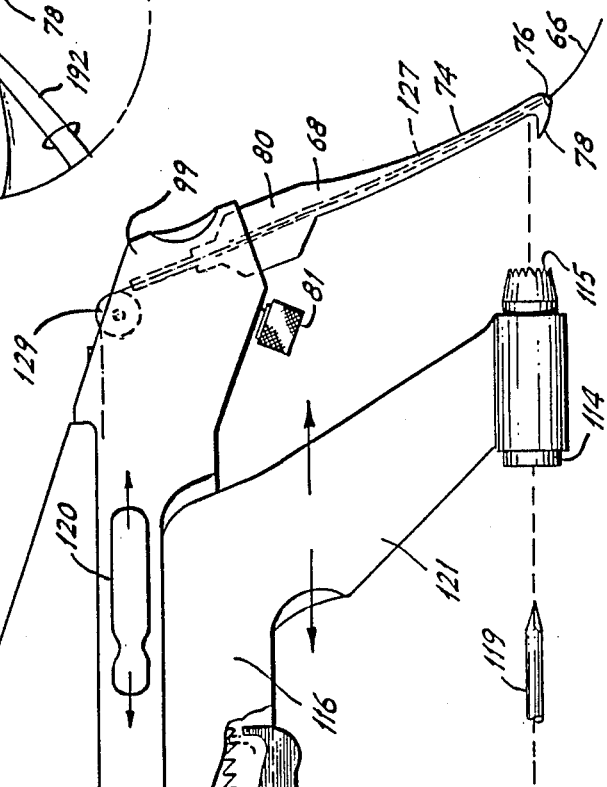
FIG. 8C is an exploded front elevational view depicting the typical positional relationships of the intra-articular portions of the tibial and frontally introduced femoral drill locating and orientation apparatus of the method of this invention, as applied to the end portions of the tibia and femur.
Figure 8B:
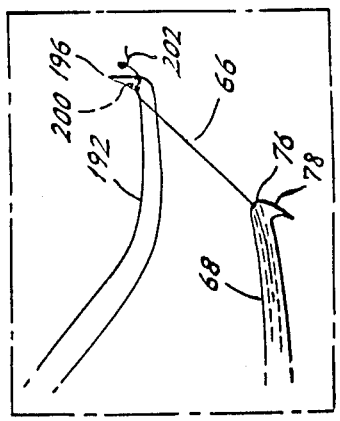
FIG. 8B is an exploded side view of the intra-articular portions of the tibial and frontally introduced femoral drill locating and orientation apparatus, showing one possible route of passage and method of fixation of a connecting wire between the two apparatus.
Figure 8A:
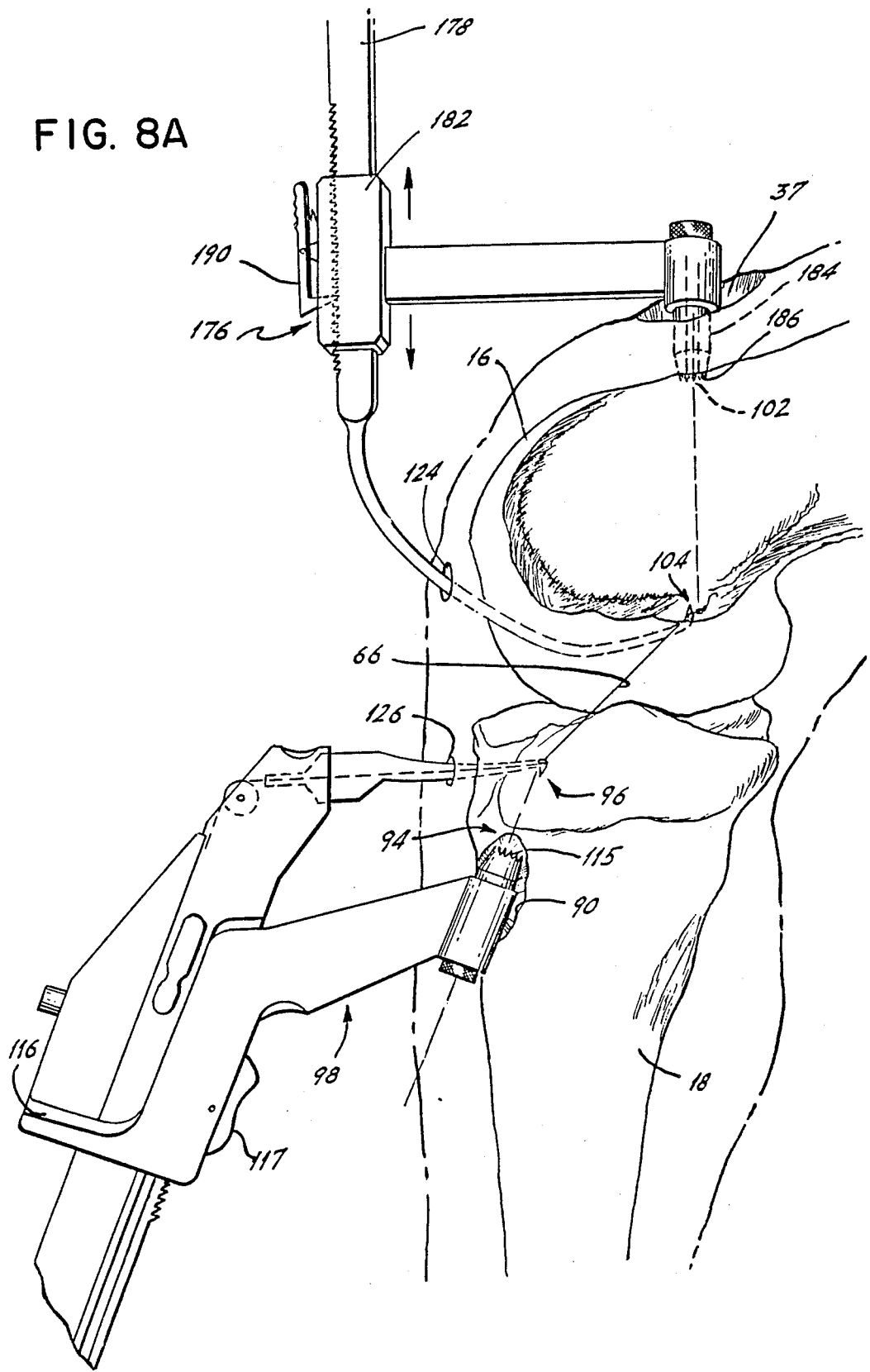
FIG. 8A is a side perspective view of a human knee joint similar to that in FIG. 2, having both the tibial and frontally introduced femoral drill locating and orientation apparatus of the method of this invention, as applied to the tibia and femur according to an alternative method of this invention.

In FIG. 8A tibial guide 98 is shown applied to tibia 18 in a typical fashion. Drill sleeve teeth 115 are in contact with tibia 18 at site 94 approaching the tibia through incision 90. Tibial aimer arm 68 extends into the knee joint via a frontal approach, through portal 126, and contacts tibia 18 at site 96 in an area approximating the connecting area of anterior cruciate ligament 24 to tibia 18.

In accordance with one method of application of one embodiment of the apparatus, anterior femoral guide 176 is mounted onto femur 16, with femoral aimer arm 192 entering intercondylar notch 28 from a medial, anterior approach. Drill sleeve teeth 186 grip the femur 16 externally at site 102, approaching the femur through incision 37. Femoral aimer arm 192 extends into intercondylar notch 28 and contacts femur 16 at site 104 in an area approximating the connecting area of anterior cruciate ligament 24 to femur 16. As with tibial guide 98, anterior femoral guide 176 includes a guide beam 178, a slidable connector 182, lock 190 and drill sleeve 184. Anterior femoral guide 176 is not equipped with a wire excursion measuring means as is tibial guide 98. However, it is possible that anterior femoral guide 176 be so equipped, with tibial guide 98 having or not having such wire excursion measuring means.

FIG. 8B shows an exploded view of tips 78 and 196 of the respective aimer arms 68 and 192. Wire 66 extends from hole 76. Tip 196 has wire passageway 200 into which the end of wire 66 is inserted. The end of wire 66 is inserted through wire passageway 200 and knotted at knot 202 thereby connecting the respective aimer arms.

FIG. 8C shows the positional relationships of aimer arms 68 and 192 with wire 66 when they are applied to the upper portion of tibia 18 and lower portion of femur 16. Wire 66 exits hole 76 in tip 78 of tibial aimer arm 68 and extends directly to tip 196 of femoral aimer arm 192, to which wire 66 is affixed. Tibial and femoral aimer arms 68 and 192 are applied to tibia 18 and femur 16 such that sites 96 and 104 (see FIG. 8A) are occupied by tips 78 and 196, respectively.

Excursion measurements and profiles may be determined from the anterior femoral guides as in the same manner as for the posterior femoral guide when determining proper femoral sites for tunnel drilling.

In one manner of applying tibial drill guide 98, one end of wire 66 is placed in tibial portal 126 and pushed within the knee joint. Conventional surgical forceps or gripping means are introduced into the knee joint through femoral portal 124 to retrieve wire 66 out through femoral portal 124. This end of wire 66 is then threaded through femoral aimer arm tip passageway 200 and knotted into knot 202 as shown in FIG. 8B. By pulling wire 66 at tibial portal 126, femoral aimer tip 196 is introduced and slid into knee joint 14 through portal 124. The end of wire 66 that exits through portal 126 is then threaded through or loaded into tibial guide 98 by way of hole 76, as hereinbefore described.

With wire 66 connecting together both aimer arms 68 and 192, anterior femoral guide 176 is applied to multiple sites on femur 16 in a region approximating the original attachment area (area B from FIG. 3) of anterior cruciate ligament 24 by embedding tip 196 into bone. Once a satisfactory site is found, drill sleeve 184 is applied by manually sliding connector 182 down guide beam 178 and engaging spring-loaded lock 190 on ratchet teeth 188.

Aimer arms 68, 82 and 192 in FIGS. 6A, 4, and 5 are constructed to allow their simultaneous use with each other within knees of all sizes. It is imperative to ensure that the tibial and femoral aimer arms do not come into contact with each other. Similarly, no aimer arm shaft may contact any bone surface in such a manner that would tend to dislodge its tip from the bone. Wire 66 must also remain free of contact with any aimer between exit hole 76 and passageway 112 or 200 when measuring wire excursion. These requirements are especially burdensome in view of the fact that spaces are very limited and that the leg may be repeatedly moved through its range of motion while the aimer arms are in use, thereby increasing the likelihood of measurement error due to inadvertent aimer arm or wire contact or tip dislodgement in the absence of precise design.

In FIG. 6A, mounting section 80 of tibial aimer arm 68 is provided for mounting on head 99 of guide beam 122. Aimer arm 68 is removable for ease of replacement in the event of damage. Curved section 74 is specifically provided with a predetermined shape to prevent contact of aimer arm 68 with the lowermost end portion of femur 16 when the knee is straightened. Aimer arm 68 has an interior channel along its entire length wide enough to transmit wire 66. This channel is not sharply angled or curved. This is necessary to allow a free longitudinal sliding of wire 66 during excursion measurement to occur with minimum friction. Previous aimers commonly have harsh angles and curves, thereby precluding free and easy excursion within them of any tension member, were they fitted with such.

In FIG. 4, femoral aimer arm 82 has curved section 90 which is specifically designed to avoid contact with the rearward, lowermost end portions of femur 16. In this way aimer arm 82 curves around the rearward aspect of the bone, with its only contact point being at tip 92.

Traditional bone tunnel drill guides are generally constructed with an aimer arm that is mounted on the guide beam in a way that causes a drill bit or drill guide pin that is positioned within the drill sleeve to be directed to the very center of the pointed tip of the aimer arm. In the present invention, this is not the case. Instead, the drill sleeve of guides 98, 33 and 176 are aligned such that the drill or drill guide pin is directed to a point that is slightly offset from the tip of each aimer arm. The direction of the offset is opposite the typical direction of the tendon graft's off center shift within the bone tunnel as it enters the joint. This offset insures proper final graft position despite its eccentric position within the bone tunnel exit. However, it is possible to not include built in offsets in the respective aimers if non-deformable grafts are employed, or grafts having non-deformable ends that are set rigidly centered within the tunnel.

It should further be appreciated that because the proper femoral site is more sensitive and much harder to determine than the tibial site, it is possible to either isometrically or physiometrically determine only the optimum femoral site in accordance with the methods of the present invention, while utilizing traditional procedures to determine the optimum tibial site. Such a procedure typically includes drilling a preliminary tunnel in the tibia and attaching an excursion gauge to a wire threaded through the tibial tunnel at that tunnel's external exit. The wire is then connected to the desired femoral guide and an excursion profile is determined in the usual manner. Although less effective, it is also possible to isometrically or physiometrically determine the optimal tibial site in accordance with the present invention and determine the femoral site in a traditional manner.

It has heretofore not been possible to determine the acceptability of the initial bone tunnel sites selected by the surgeon prior to drilling some type of bone channels at those sites. Now, if the mechanical behavior of the tendon graft, as predicted by the drill guides described herein, differs significantly from that desired by the surgeon be it isometric or physiometric, the surgeon may repeatedly test different prospective tunnel sites before drilling until the desired points are determined.

Although this invention has been described in connection with specific forms thereof, it will be appreciated that a wide array of equivalents may be substituted for the specific elements shown and described herein without departing from the spirit and scope of this invention as described in the appended claims.

We claim:

1. In a method for replacing a ligament in a joint connecting pivotable bones to one another, the steps which comprise:
    (a) selecting proposed ligament attachment sites for both of said bones;
    (b) applying a test ligament to said sites;
    (c) pivoting said bones and determining the resulting shortening-lengthening profile relationship;
    (d) comparing the resulting shortening-lengthening profile relationship with the optimum shortening-lengthening profile relationship;
    (e) repeating if necessary, steps (a) through (d), until optimum attachment sites have been determined against the optimum shortening-lengthening profile relationship; and
    (f) attaching a replacement ligament to said optimum sites.

2. A method as defined in Claim 1 wherein said optimum shortening-lengthening profile relationship closely approximates the physiologic shortening-lengthening profile occuring in a natural ligament in said joint over a similar range of pivoting motion.

3. A method a defined in Claim 1 wherein said replacement can be performed arthroscopically or through traditional open joint incisions.

4. A method as defined in Claim 1 wherein said replacement ligament is attached by drilling tunnels in said bones between said optimum attachment sites and threading said replacement ligament therethrough.

5. A method as defined in Claim 4 wherein said replacement ligament is secured into said bones by surgical staples or screws.

6. A method as defined in Claim 1 wherein said optimum shortening-lengthening profile relationship closely approximates the isometric shortening-lengthening profile occuring in a natural ligament in said joint over a similar range of pivoting motion.

7. A method of surgery for reconstruction of a ligament in a joint having two swingable bones which method comprises;
    preliminarily marking a first tunnel end site at a point on the end of a first of said bones within said joint;
    preliminarily marking a second tunnel end site at a point on said first one of said bones away from said joint, said end sites on said first one of said bones defining a path for a tunnel therebetween;
    preliminarily marking a third tunnel end site at a point on the end of a second one of said bones within said joint;
    preliminarily marking a fourth tunnel end site at a point on said second one of said bones away from said joint, said end sites on said second one of said bones defining a path for a tunnel therebetween;
    connecting excursion measuring means between said first and third tunnel end sites within said joint;
    flexing said bones in said joint over a substantially full range of motion and repeatedly adjusting the location of any or all of said tunnel end sites until the change in separation distance between sites as measured said by said excursion measuring means approximates the natural physiometric shortening-lengthening experimental by the naturally occurring ligament in said joint over a similar range of motion;

drilling a tunnel in each of said bones between physiometrically determined tunnel end sites; and threading a replacement ligament into said tunnels and securing said ligament to said bones.

8. A method as defined in Claim 7 wherein said surgery is performed arthroscopically.

9. A method as defined in Claim 7 which further comprises clearing away the damaged natural ligament and any mensical debris prior to preliminarily marking said tunnel end sites.

10. A method as defined in Claim 7 which further comprises widening said intercondylar notch by abrasion prior to preliminarily marking said tunnel end sites.

11. A method as defined in Claim 7 wherein said ligament is secured to said bones with surgical staples or screws.

12. A method of surgery for reconstruction of a ligament in a joint having two swingable bones which method comprises:

preliminarily marking a first tunnel end site at a point on the end of a first of said bones within said joint;

preliminarily marking a second tunnel end site at a point on said first one of said bones away from said joint, said end sites on said first one of said bones defining a path or a tunnel therebetween;

preliminarily marking a third tunnel end site at a point on the end of a second one of said bones within said joint;

preliminarily marking a fourth tunnel end site at a point on said second one of said bones away from said joint, said end sites on said second one of said bones defining a path for a tunnel therebetween;

connecting excursion measuring means between said first and third tunnel end sites within said joint;

flexing said bones in said joint over a substantially full range of motion and repeatedly adjusting the location of any or all of said tunnel end sites until the change in separation distance between sites as measured said by said excursion measuring means approximates the natural isometric shortening-lengthening experimental by the naturally occurring ligament in said joint over a similar range of motion;

drilling a tunnel in each of said bones between isometrically determined tunnel end sites; and threading a replacement ligament into said tunnels and securing said ligament to said bones.

* * * * *